United States Patent [19]

Myers

[11] 3,979,333

[45] Sept. 7, 1976

[54] ACTIVATING GROUP VIII METAL/ALUMINA CATALYSTS WITH HYDROGEN HALIDE/HALOSILANE/ORGANIC HALIDE

[75] Inventor: John W. Myers, Bartlesville, Okla.

[73] Assignee: Phillips Petroleum Company, Bartlesville, Okla.

[22] Filed: Feb. 3, 1975

[21] Appl. No.: 546,820

[52] U.S. Cl............................. 252/441; 252/442; 260/683.75; 260/683.68; 208/111
[51] Int. Cl.[2]..................... B01J 27/08; B01J 27/10
[58] Field of Search............................ 252/442, 441

[56] References Cited
UNITED STATES PATENTS 3,449,264 6/1969 Myers ................................. 252/441
3,661,770 5/1972 Givens ............................ 252/442 X Primary Examiner—Patrick P. Garvin

[57] ABSTRACT

A catalyst comprising a Group VIII metal selected from Pt, Ir, Os, Ru, Rh, or Pd supported on alumina is activated at an elevated temperature with an activating gas comprising a hydrogen halide such as HCl, a halosilane such as silicon tetrachloride, and an organic halide such as ethyl chloride. The resulting catalysts exhibit an outstandingly high isomerization rate constant in the isomerization of feedstocks such as n-butane to isobutane.

12 Claims, No Drawings

ACTIVATING GROUP VIII METAL/ALUMINA CATALYSTS WITH HYDROGEN HALIDE/HALOSILANE/ORGANIC HALIDE

BACKGROUND OF THE INVENTION

This invention relates to activating catalysts of selected Group VIII metals on alumina.

Platinum supported on alumina has long been used as an isomerization catalyst. It is broadly known to treat such materials with halogens to activate same. Myers, U.S. Pat. No. 3,449,264 issued June 10, 1969, broadly discloses activation utilizing certain halogens and/or halides such as HCl for activating alumina catalysts.

SUMMARY OF THE INVENTION

It is an object of this invention to provide a hydrocarbon conversion catalyst of improved activity;

it is a further object of this invention to provide a process for activating a platinum group metal/alumina catalyst utilizing a combination of a halosilane and an organic halide;

it is yet a further object of this invention to provide a platinum group metal/alumina catalyst which is applicable to commercial scale operation; and it is yet a further object of this invention to provide a catalyst capable of effecting isomerization at a higher rate constant.

In accordance with this invention a catalyst of Pt, Ir, Os, Ru, Rh, or Pd on alumina is activated in the presence of a hydrogen halide selected from hydrogen chloride and hydrogen bromide in combination with a halosilane selected from chlorosilanes and bromosilanes and an organic halide selected from organic chlorides and organic bromides.

DESCRIPTION OF THE PREFERRED EMBODIMENTS

The catalysts which are activated in accordance with this invention are basically a selected Group VIII metal supported on an active alumina base. The applicable Group VIII metals are at least one of platinum, iridium, osmium, palladium, rhodium, and ruthenium. This class of catalyst is well known in the prior art and generally contains from 0.01 to 10, preferably 0.1 to 1, weight percent metal based on the total catalyst weight including the alumina base. The preferred metal is platinum. These catalysts can also contain minor amounts of a halogen incorporated during preparation of the catalyst, chlorine being the halogen most commonly present. Although one or both of these halogens can be present in the catalyst prior to activation by the process of the present invention, the catalyst containing them is not the equivalent of a catalyst which has been activated by the present process. The amount of halogen in the catalyst as prepared (i.e., prior to activation in accordance with this invention) if any, is usually less than about 1.5 weight percent based on the total weight of the catalyst.

To produce these catalysts, an alumina, well known in the art as an "active" alumina is essential. Active aluminas may be synthetically prepared as by calcination of alumina gels which are formed by adding such reagents as ammonium hydroxide to a salt of aluminum, such as aluminum chloride or aluminum nitrate. These aluminas are generally gamma or eta aluminas depending upon the dehydrating conditions used. Similar active aluminas may be prepared by calcination of naturally occurring aluminas such as the monohydrate and the trihydrate. Bauxite is a common source of active alumina when properly calcined and dehydrated. The alumina base of the catalyst may contain minor amounts of silica and boron oxide. The amounts of these materials should be less than about 30 percent, preferably less than about 10 weight percent of the catalyst base component to produce the most active catalyst.

The hydrogen halide is HCl or HBr, most preferably anhydrous HCl.

The halosilane is preferably a chlorosilane, which can be represented by the formula $SiX_4$ in which each X can be the same or different and where at least one X is chlorine and the other X substituents are selected from the group consisting of chlorine, hydrogen, and alkyl radicals containing from 1 to 3 carbon atoms per molecule. Exemplary compounds include silicon tetrachloride, trichlorosilane, monochlorosilane, trichloromethylsilane, dichloropropylsilane and the like. A presently preferred compound based on cost and availability is silicon tetrachloride. The corresponding bromosilanes can also be used.

When a hydrogen halide is used in the activating gas along with a halosilane, it is preferred that the halogens in each compound be the same. That is, a combination consisting of silicon tetrachloride and hydrogen chloride is preferred rather than silicon tetrachloride and hydrogen bromide, for example.

The organic halide is preferably a chlorinated paraffin containing from 1 to 3 carbon atoms per molecule. Exemplary compounds include methylene chloride, ethyl chloride, isopropyl chloride, chloroform, carbon tetrachloride, and the like. The corresponding bromine compounds can also be used.

The Pt, Ir, Os, Ru, Rh, or Pd metal on alumina catalyst is first calcined in a manner known in the art, for instance, by heating to a temperature within the range of 500° to 900° F., more preferably 700° to 900° F., for a time within the range of 1 to 10, preferably 1 to 3, hours. Preferably, this is carried out in the presence of air although air is not essential.

The catalyst is then heated to the activation temperature which is generally within the range of 500° to 1600° F., preferably 900° to 1500° F., still more preferably 1200° to 1500° F. The catalyst may then be held within this temperature range for a time of at least 10 minutes, preferably at least 1 hour. A range of 1.5 to 15, more preferably 1.5 to 5, hours is satisfactory. This step of holding the catalyst at activation temperature is primarily for the purpose of being sure the catalyst is dry.

The catalyst is then treated with a dry activating gas comprising the hydrogen halide plus the combination of a halosilane and an organic halide. The temperature during this treatment is still within the same range of 500° to 1600°, preferably 900° to 1500°, more preferably 1200° to 1500° F. Time for this treatment is normally within the range of 0.1 to 10, preferably 1 to 3, hours. After this treatment, the thus-activated catalyst is cooled, for instance, to ambient temperature. The heating, holding at activation temperature, activation, and cooling can be carried out in an inert atmosphere such as under nitrogen, or more preferably in the presence of hydrogen. A mixture of nitrogen and hydrogen can be utilized or pure hydrogen. Preferably a small amount of hydrogen halide, i.e. 1–20 mole percent, is added to the nitrogen, hydrogen, or hydrogen-nitrogen mixture during cooling.

The concentration of the halosilane and the organic halide in the activating ambient are preferably in the range of about 0.05 to about 10 weight percent each of the halosilane and organic halide based on the weight of the hydrogen halide. A more preferred range is about 0.1 to about 5 weight percent each. The weight ratio of the halosilane to the organic halide can be within the range of 0.1:1 to 10:1. A relatively high ratio of the organic halide is preferred since one very beneficial aspect of the invention is the ability to achieve improved results with only a small amount of halosilane (thus reducing any silicon deposit on the catalyst) by utilizing a mixture of the halosilane and the organic halide. Good results have been obtained when the weight ratio of halosilane to organic halide ranges from about 0.3:1 to about 1:1.

As noted hereinabove, hydrogen is preferably present during the activation step at least. In instances where hydrogen is present, it can be present in an amount within the range of 1 to 95 mole percent based on the moles of hydrogen halide.

The activating ambient is contacted with the catalyst in an amount effective to increase the halogen content of the catalyst and to increase the activity of the catalyst. The amount of halogen incorporated by this technique will generally be within the range of 1 to 10, preferably 2 to 6, weight percent based on the weight of the Group VIII metal-alumina composite.

The catalyst of the present invention are particularly applicable to the skeletal isomerization of isomerizable hydrocarbons including acyclic paraffins, and naphthenes. These catalysts are particularly suitable for the isomerization of straight chain or singly-branched paraffins containing four to eight carbon atoms per molecule including n-butane, n-pentane, n-heptane, methylpentane, and the like. Some examples of naphthenes which can be isomerized with these catalysts are methylcyclopentane, dimethylcyclopentane, cyclohexane, methylcyclohexane, and the like. Actually, these are equilibrium reactions as follows:

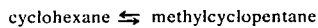

cyclohexane ⇌ methylcyclopentane

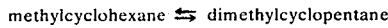

methylcyclohexane ⇌ dimethylcyclopentane

pentane ⇌ methylbutane

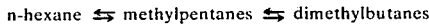

n-hexane ⇌ methylpentanes ⇌ dimethylbutanes

Conditions can be adjusted to give hydrocracking, as for instance to produce butane from n-octane.

The isomerization reaction conditions and recovery procedures can be varied to achieve the desired conversion in a manner known in the art. Isomerization of normal butane to isobutane is one presently referred application.

Hydrocarbons to be isomerized are contacted with the activated catalysts prepared in accordance with the invention at an isomerization temperature of about 100°–600° F., more preferably 150°–450° F., in the presence of free hydrogen. The hydrogen-hydrocarbon mol ratios normally used during isomerization are within the range of about 0.25 to 10 to insure long catalyst life. Liquid hourly space velocities, i.e., the volume of liquid charge per hour per volume of catalyst, of about 0.1 to 15 are satisfactory and pressures within the range of atmospheric to 1500 psig in the isomerization zone are suitable.

Maintenance of catalyst activity during the isomerization process is aided by the inclusion of 0.001 to about 1 weight percent chloride in the feed in the form of chlorinated hydrocarbon promoters such as carbon tetrachloride, chloroform, ethyl chloride, isopropyl chloride, etc. This is not a substitute for the activation of the catalyst but it aids in maintaining over long process periods the high level of activity of the invention catalysts.

The isomerization process can be carried out either in a batchwise or continuous basis, preferably the latter. In a continuous process it is to be understood that hydrogen in the effluent product can be separated and recycled and that recycling of isomerization promoters, if employed, can be practiced. These catalysts are also suitable for hydrocracking operations.

EXAMPLE

A gamma-alumina in the form of 1/16 inch diameter extrudate was impregnated with an aqueous solution of chloroplatinic acid and hydrochloric acid sufficient to give a platinum content of 0.37 weight percent and a chloride content of 1.25 weight percent based on the calcined composite. The impregnated sample was dried in air at 240° F. and calcined in air at 800° F. for 2 hours. Equal portions by weight were taken from the calcined catalyst and each portion was heated for two hours in a hydrogen atmosphere followed by activation at about 1250° F. in the medium chosen for 2 hours as shown in the Table. After activation each catalyst was removed from the furnace in its quartz tube, cooled in the activating ambient to about 200° F. (12–13 minutes) and transferred to a reactor for testing. The isomerization tests were conducted at about 305°–325° F. at a space velocity of 4 parts liquid feed per part catalyst per hour (by volume, LHSV), 500 psig and a 0.5 hydrogen/feed mole ratio. The feed tested was n-butane containing about 200 ppm chloride as carbon tetrachloride. The results are presented in the Table.

TABLE

Effect of Promoting Halide-Containing Compounds On Isomerization Activity of Treated Catalysts

| Run No. | Promoter Added To[a] HCL–H₂ Activating Gas, Wt. % of HCl | Isomerization Results at 305–325° F. | |
|---|---|---|---|
| | | Isobutane in C₄ Effluent Mole % | Relative[b] Rate Constant |
| 1 | None | 53.3 | 1.09 |
| 2 | 1.2 SiCl₄ | 58.0 | 1.40 |
| 3 | 2.8 SiCl₄ | 58.0 | 1.40 |
| 4 | 1.9 ethyl chloride | 57.4 | 1.36 |
| 5 | 3.8 ethyl chloride | 56.7 | 1.30 |
| 6 | 0.2 SiCl₄ + 1.1 ethyl chloride | 56.8 | 1.31 |
| 7 | 0.4 SiCl₄ + 1.1 ethyl chloride | 59.3 | 1.52 |
| 8 | 0.9 SiCl₄ + 1.1 ethyl chloride | 58.7 | 1.47 |

TABLE-continued

Effect of Promoting Halide-Containing Compounds
On Isomerization Activity of Treated Catalysts

| Run No. | Promoter Added To[a] HCl—H$_2$ Activating Gas, Wt. % of HCl | Isomerization Results at 305–325° F. | |
|---|---|---|---|
| | | Isobutane in C$_1$ Effluent Mole % | Relative[b] Rate Constant |
| 9 | ≠0.7 SiCl$_4$[c] + 1.9 ethyl chloride | 60.6 | 1.67 |
| 10 | 0.7 SiCl$_4$ + 1.9 ethyl chloride | 58.3 | 1.43 |

[a]Unpromoted ambient consisted of 62 mole percent HCl and 38 mole percent H$_2$. The activation gas flow was 29 liters per hour at STP. The SiCl$_4$ was added by passing a portion of the H$_2$ through the silicon tetrahalide. The ethyl chloride was metered into the gas stream by means of a rotameter.
[b]Calculated from the test results using the first order reversible reaction kinetic equations presented on pages 62–63 of "Chemical Reaction Engineering" Levenspiel, John Wiley & Sons, 1962, Library of Congress Catalog No. 62 15185.
[c]Less precise balance used in weighing. The actual amount is believed to be between about 0.4 and 0.7 weight percent.

Inspection of the results shows that the isomerization activity of the catalyst is improved when small amounts of silicon tetrachloride or ethyl chloride are present in the activating gas along with hydrogen chloride. Run 5 suggests that about 4 weight percent ethyl chloride is somewhat less effective than the about 2 weight percent used in Run 4. The combinations of silicon tetrachloride and ethyl chloride shown in Runs 6–10 are generally more effective than about equal weights of either component alone when the amount of silicon tetrachloride exceeds about 0.2 weight percent.

While this invention has been described in detail for the purpose of illustration, it is not to be construed as limited thereby but is intended to cover all changes and modifications within the spirit and scope thereof.

What is claimed is:

1. A method for activating an alumina supported Pt, Ir, Os, Ru, Rh, or Pd metal catalyst which comprises:
   heating said catalyst at a temperature within the range of 500° to 1600° F.;
   contacting said catalyst at said temperature of 500° to 1600° F. with a dry activating gas comprising a hydrogen halide selected from the group consisting of HCl and HBr, a halosilane selected from the group consisting of chlorosilanes and bromosilanes, and an organic halide selected from the group consisting of chlorinated paraffins and brominated paraffins for a time sufficient to impart a halide content to the catalyst and to increase the activity of the catalyst, the weight ratio of said halosilane to said organic halide being within the range of 0.1:1 to 10:1; and
   thereafter cooling said thus-contacted catalyst.

2. A method according to claim 1 wherein said temperature is within the range of 1200° to 1500° F. and said contacting is carried out for a time within the range of 0.1 to 10 hours.

3. A method according to claim 1 wherein said hydrogen halide is anhydrous hydrogen chloride, said halosilane is a chlorosilane of the formula SiX$_4$ in which each X can be the same or different and wherein at least one X is chlorine and the other X substituents are selected from the group consisting of chlorine, hydrogen, and alkyl radicals containing from 1 to 3 carbon atoms per molecule, and said organic halide is a chlorinated paraffin containing from 1 to 3 carbon atoms per molecule.

4. A method according to claim 3 wherein said chlorosilane is silicon tetrachloride and said chlorinated paraffin is ethyl chloride.

5. A method according to claim 1 wherein said activating gas is carried by a stream of hydrogen.

6. A method according to claim 1 wherein said metal is platinum.

7. A method according to claim 1 wherein said alumina supported metal catalyst is held at said temperature of 500° to 1600° F. for a time within the range of 1.5 to 15 hours after said heating and before said contacting.

8. A method according to claim 1 wherein said metal is platinum and is present in an amount within the range of 0.1 to 1 weight percent based on the weight of said catalyst, said hydrogen halide is anhydrous HCl, said halosilane is silicon tetrachloride, said organic halide is ethyl chloride, and said activating gas is carried by a stream of hydrogen.

9. A method according to claim 8 wherein said temperature is within the range of 1200° to 1500° F.

10. A method according to claim 9 wherein the weight ratio of silicon tetrachloride to ethyl chloride ranges from 0.3:1 to 1:1 and wherein said silicon tetrachloride and ethyl chloride are each present in an amount within the range of 0.05 to 10 weight percent based on the weight of said anhydrous HCl.

11. A catalyst produced by the method of claim 10.

12. A catalyst produced by the method of claim 1.

* * * * *